United States Patent [19]
Hill et al.

[11] 4,200,738
[45] Apr. 29, 1980

[54] METHOD FOR PREPARING AURANOFIN

[75] Inventors: David T. Hill, North Wales; Blaine M. Sutton, Hatboro, both of Pa.; Ivan Lantos, Blackwood, N.J.

[73] Assignee: SmithKline Corporation, Philadelphia, Pa.

[21] Appl. No.: 789,602

[22] Filed: Apr. 21, 1977

[51] Int. Cl.² ............................................ C07H 23/00
[52] U.S. Cl. ..................................... 536/121; 536/122
[58] Field of Search ............................ 536/4, 121, 122

[56] References Cited

U.S. PATENT DOCUMENTS 3,635,945  1/1972  Nemeth et al. ...................... 536/121

OTHER PUBLICATIONS

Sutton, "Jour. of Medicinal Chem.," vol. 15, No. 11, 1972, pp. 1095–1098.

*Primary Examiner*—Johnnie R. Brown
*Attorney, Agent, or Firm*—William H. Edgerton

[57] ABSTRACT

A new synthesis of auranofin comprising reacting 2,3,4,6-tetra-O-acetyl-α-D-glucopyranosyl bromide with a S-(triethylphosphineaurous)thiouronium salt.

4 Claims, No Drawings

METHOD FOR PREPARING AURANOFIN

This invention comprises a new chemical method for preparing auranofin which uses a 2, 3, 4, 6-tetra-O-acetylglucopyranosyl reactive ester such as a bromide or chloride with a S-(triethylphosphineaurous) thiouronium salt in an alkaline reaction medium.

Auranofin is an orally active therapeutic agent which is useful in man as an antiarthritic [J. Med. Chem. 15, 1095 (1972); U.S. Pat. No. 3,635,945].

The synthetic process here described and claimed is represented by the following diagram:

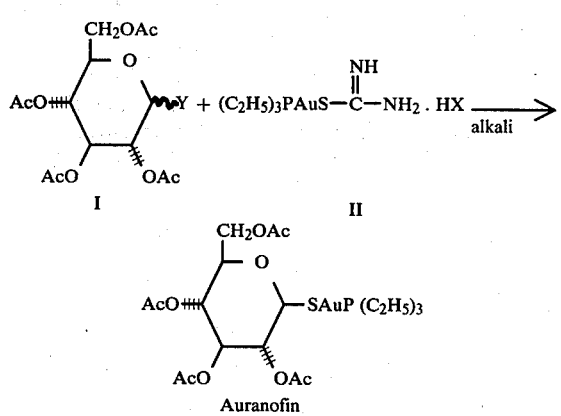

In the reaction sequence above Y is a reactive ester residue leaving group such as a reactive halo for example chloro or bromo or an aryl or lower alkylsulfonyloxy such as tosyloxy (p-toluenesulfonyloxy), brosyloxy (p-bromophenylsulfonyloxy), trifluoromethanesulfonyloxy or mesyloxy (methanesulfonyloxy); Ac is acetyl and HX is the acid portion of the thiouronium salt preferably a commonly used mineral acid such as hydrogen chloride, bromide or iodide, monohydrogen sulfate, nitric acid etc. Preferably for convenience Y is chloro or bromo.

The configuration at the 1-position of the sugar starting materials (I) is indicated to be either α or β. Those skilled in the art will recognize the displacement of a α-halo will give the desired β-configuration which is present in auranofin (SN2). The sulfur containing ester starting materials such as tosyloxy on the other hand will be in the β-configuration since one can expect no change in configuration upon reaction to give auranofin (SN1).

The term "leaving group" is that defined in the art as the weakly basic ionic group which is displaced by a nuclephilic group which in this case is triethylphosphinegoldthio group. See Organic Chemistry, Morrison and Boyd, 3rd Ed. (1973). As defined above the leaving group is a reactive halo or sulfonyloxy moiety generated during the nucleophilic substitution by the tertiary-phosphinegoldthio portion of the thiouronium complex (II).

The reaction of this invention is conveniently carried out by reacting approximately equimolar quantities of the glucose ester (I) and the thiouronium salt (II) or a slight excess of the latter in the presence of at least two molar equivalents of alkali in a water miscible inert solvent in which the reactants are soluble. The alkali can be any of those commonly used in organic synthesis such as alkali metal carbonates, bicarbonates or hydroxides. Most conveniently sodium or potassium carbonate or bicarbonate is used.

The solvent system is most conveniently an aqueous lower alkanol such as aqueous methanol, ethanol or isopropanol or aqueous acetone. Other water miscible solvents also may be used such as dimethylsulfoxide, dimethylacetamide or dimethylformamide. Alternatively a biphasic organic/water system can be used such as a halohydrocarbon/water system optionally with the addition of a phase transfer catalyst such as a Crown ether.

The reaction is most conveniently carried out at from about 0° to room temperature but will also proceed at up to the boiling point of the reaction mixture. If a high boiling solvent is used temperatures up to about 75° are sufficient for reaction. The reaction usually proceeds quickly at the preferred temperatures, within ½-2 hours but is allowed to course to go to completion which may vary with the choice of reactants, temperatures or solvent systems.

The starting materials for the reaction are either known in the art or are easily prepared by prior art reactions. For example 2,3,4,6-tetra-O-acetyl-α-D-glucopyranosyl halides are reported in Methods in Carbohydrate Chemistry, Vol. 2, page 434 (1963) R. L. Whistler et al. Representative tosyl, mesyl, brosyl and trifluoromethylmethanesulfonyl esters of 2,3,4,6-tetra-O-acetylglucose are prepared by general synthetic methods described in the Advances in Carbohydrate Chemistry, Vol. 8, Academic Press (1935) page 111. The tertiary-phosphinegold halides are reported in B. M. Sutton et al. J. Med. Chem. 15, 1095 (1972). These are condensed with thiourea to prepare the thiouronium salts. Other salts (HX in II) may be prepared by standard reaction for forming various salts.

The reaction product is isolated by methods standard in the art.

The following examples are designed to teach the practice of this invention but not to limit its scope. All temperatures are Centigrade.

EXAMPLE 1

A solution of 4.0 g (11.4 mmole) of triethylphosphinegold chloride and 0.86 g (11.2 mmole) of thiourea in 80 ml of acetone was stirred overnight at room temperature. The precipitate was removed by filtration and washed with acetone to give S-(triethylphosphineaurous)thiouronium chloride, m.p. 140°-143°. The bromide is described by G. E. Coates et al., Aust. J. Chem. 19, 536 (1966) and may also be used as starting material.

A solution of 1.3 g (9.4 mmoles) of potassium carbonate in water (10 ml) was added to 2.0 g (4.7 mmoles) of S-(triethylphosphinoaurous) thiouronium chloride in water (30 ml) kept at 0° followed immediately by the addition of 1.9 g (4.6 mmoles) of 2,3,4,6-tetra-O-acetyl-α-D-glucopyranosyl bromide in acetone (20 ml). After stirring one hour at room temperature the mixture was diluted with water (100 ml) and extracted with chloroform (3×30 ml). The combined chloroform extracts was dried over magnesium sulfate, filtered and the solvent removed at reduced pressure to give an oil product. Chromatography (silica gel/chloroform) gave a viscous oil which was purified further by preparative thin layer chromatography (silica gel/ether) to give auranofin, m.p. 100°-104°; $[\alpha]_D^{25}$ (1% methanol)$= -47.8°$.

Substituting 2,3,4,6-tetra-O-acetyl-α-D-glucopyranosyl bromide also gives auranofin. Substituting 1-β-tosyloxy-2,3,4,5-tetra-O-acetylglucose, prepared by reacting tosylchloride with 2,3,4,6-tetraacetyl-β-glucose in pyridine, gives auranofin.

What is claimed is:

1. The method of preparing auranofin comprising reacting a S-(triethylphosphineaurous) thiouronium salt with a compound of the structure:

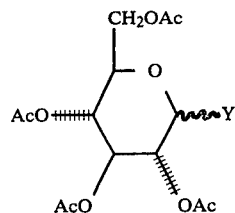

in which Ac is acetyl and Y is bromo, chloro, tosyloxy, brosyloxy, mesyloxy or trifluoromethanesulfonyloxy, in an alkaline media in which the reactants are soluble.

2. The method of claim 1 in which Y is α-bromo or α-chloro.

3. The method of claim 2 in which Y is α-bromo; the media is aqueous acetone in the presence of an excess of an alkali metal carbonate or bicarbonate and the thiouronium salt is the chloride, bromide or iodide.

4. The method of claim 1 in which Y is tosyloxy.

* * * * *